US009931605B2

(12) United States Patent
Carroll et al.

(10) Patent No.: US 9,931,605 B2
(45) Date of Patent: Apr. 3, 2018

(54) CONTROLLED DISSOLUTION SOLID PRODUCT DISPENSER

(71) Applicant: ECOLAB USA INC, St. Paul, MN (US)

(72) Inventors: Richard R. Carroll, Blaine, MN (US); John D. Morey, St. Paul, MN (US); Andrew Schultz, Minneapolis, MN (US); Ryan Drake, White Bear Lake, MN (US); John E. Thomas, River Falls, WI (US); Troy A. Anderson, Eagan, MN (US); Joshua J. Lanz, West St. Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 15/377,710

(22) Filed: Dec. 13, 2016

(65) Prior Publication Data

US 2017/0151539 A1 Jun. 1, 2017

Related U.S. Application Data

(63) Continuation of application No. 14/577,559, filed on Dec. 19, 2014, now Pat. No. 9,550,154, which is a (Continued)

(51) Int. Cl.
*A61L 2/00* (2006.01)
*B01D 11/04* (2006.01)
(Continued)

(52) U.S. Cl.
CPC ........ *B01F 15/0022* (2013.01); *B01F 1/0022* (2013.01); *B01F 15/0037* (2013.01); *B01F 2215/004* (2013.01)

(58) Field of Classification Search
CPC ..... A61L 2/00; B01F 1/00; B05D 1/00; C02F 1/00
(Continued)

(56) References Cited

U.S. PATENT DOCUMENTS 5,089,127 A 2/1992 Junker et al.
5,133,381 A 7/1992 Wood et al.
(Continued)

FOREIGN PATENT DOCUMENTS

DE 4336339 A1 4/1995
EP 0 225 859 * 6/1987 ............. A47L 15/44
(Continued)

OTHER PUBLICATIONS

Ecolab USA Inc. et al., PCT/US2013/026892 filed Feb. 20, 2013, Notification of Transmittal of The International Search Report and The Written Opinion of The International Searching Authority, or The Declaration, dated Jul. 23, 2013.
(Continued)

*Primary Examiner* — Monzer R Chorbaji
(74) *Attorney, Agent, or Firm* — McKee, Voorhees & Sease, PLC

(57) ABSTRACT

A method, apparatus, and system for obtaining a solution from a solid product are disclosed. A solid product is housed in a dispenser. A liquid is introduced into the housing of the dispenser to interact with the solid product to form a solution. To control the concentration of the formed solution, the turbulence of the liquid introduced to the dispenser is controlled and adjusted either manually or on a real time basis to account for varying characteristics of either or both of the solid product and the liquid. The dispenser will adjust the turbulence based on the characteristics to maintain a formed solution within an acceptable range of concentration. The concentrated solution can then be discharged from the dispenser to an end use application.

20 Claims, 9 Drawing Sheets

Related U.S. Application Data continuation of application No. 13/771,351, filed on Feb. 20, 2013, now Pat. No. 8,945,476.

(60) Provisional application No. 61/601,176, filed on Feb. 21, 2012.

(51) Int. Cl.

| | |
|---|---|
| ***B01D 11/02*** | (2006.01) |
| ***C02F 1/68*** | (2006.01) |
| ***B08B 9/00*** | (2006.01) |
| ***B01F 15/00*** | (2006.01) |
| ***B01F 1/00*** | (2006.01) |

(58) Field of Classification Search

USPC ........... 137/2; 222/320; 422/1, 28, 255–256, 422/261, 292; 210/749; 134/22.16, 134/22.17

See application file for complete search history.

(56) References Cited

U.S. PATENT DOCUMENTS

| | | | |
|---|---|---|---|
| 5,389,344 | A | 2/1995 | Copeland et al. |
| 5,427,748 | A | 6/1995 | Wiedrich et al. |
| 5,494,644 | A | 2/1996 | Thomas et al. |
| 5,505,915 | A | 4/1996 | Copeland et al. |
| 5,810,043 | A | 9/1998 | Grenier |
| 5,928,608 | A | 7/1999 | Levesque et al. |
| 6,423,280 | B1 | 7/2002 | Tarara et al. |
| 7,325,747 | B2 | 2/2008 | Jonte |
| 7,597,861 | B2 | 10/2009 | Thomas et al. |
| 7,913,926 | B2 | 3/2011 | Goncze |
| 7,988,065 | B2 | 8/2011 | Spinelli et al. |
| 8,945,476 | B2 | 2/2015 | Carroll |
| 2005/0201200 | A1 | 9/2005 | Fleig |
| 2005/0258258 | A1 | 11/2005 | Jonte |
| 2006/0231683 | A1 | 10/2006 | Orr |
| 2007/0253876 | A1 | 11/2007 | Limback et al. |

FOREIGN PATENT DOCUMENTS

| | | |
|---|---|---|
| EP | 0225859 A2 | 6/1987 |
| EP | 1157230 | 5/2006 |
| EP | 2169511 | 3/2010 |
| GB | 2467064 | 7/2010 |

OTHER PUBLICATIONS

European Patent Office, “Extended European Search Report”, issued in connection with International Application PCT/US2013026892, 7 pages, dated Oct. 7, 2015.

* cited by examiner

CONTROLLED DISSOLUTION SOLID PRODUCT DISPENSER

CROSS-REFERENCE TO RELATED APPLICATIONS

This application is a Continuation Application of U.S. application Ser. No. 14/577,559, filed Dec. 19, 2014, which is a Continuation Application of U.S. application Ser. No. 13/771,351, filed Feb. 20, 2013, now Pat. No. 8,945,476, issued on Feb. 3, 2015, which claims priority under 35 U.S.C. § 119 to provisional application Ser. No. 61/601,176 filed Feb. 21, 2012, all of which are herein incorporated by reference in their entirety.

FIELD OF THE INVENTION

The present invention relates generally to a dispenser and method of operating for dispensing a solution from a solid product. More particularly, but not exclusively, the invention relates to a method and apparatus for controlling the concentration of the dispensed solution created by combining a solid product with a liquid.

BACKGROUND OF THE INVENTION

Dissolution parameters of a solid product into a liquid solution, such as a liquid detergent used for cleaning and sanitizing, change based on the operating parameters of and inputs to the dissolution process. Spraying liquid onto a solid product to dissolve it into a liquid solution is one technique. With this technique, the operating parameters change in part based on characteristics within the dispenser, such as the distance between the solid product and the spray nozzle and the change in the pressure and temperature of the liquid being sprayed onto the solid product. Changes in a nozzle's flow rate, spray pattern, spray angle, and nozzle flow can also affect operating parameters, thereby affecting the chemistry, effectiveness, and efficiency of the concentration of the resulting liquid solution. In addition, dissolution of a solid product by spraying generally requires additional space within the dispenser for the nozzles spray pattern to develop and the basin to collect the dissolved product, which results in a larger dispenser.

Therefore, there exists a need in the art for a dispenser having the capability to adjust the flow scheme or turbulence of a liquid contacting a solid product based on a characteristic of either an uncontrolled parameter or condition, such as an environmental condition or a condition of the solid product to maintain a dispensed solution having a concentration within an acceptable range. There also exists a need to update the turbulence based upon the dispensing concentration.

SUMMARY OF THE INVENTION

Therefore, it is principal object, feature, and/or advantage of the present invention to provide an apparatus that overcomes the deficiencies in the art.

It is an object, feature, and/or advantage of the present invention to provide a method and dispenser for producing a solution from a solid product that maintains a desired concentration of the solution.

It is another object, feature, and/or advantage of the present invention to provide a dispenser that will adjust the flow turbulence of a liquid in contact with a solid product based upon a characteristic of the turbulence or product to result in a desired concentration.

It is yet another object, feature, and/or advantage of the present invention to provide a method of forming a solution from a solid product and a liquid that increases the likelihood that the solution will be within a desired concentration.

It is a further object, feature, and/or advantage of the present invention to provide a dispensing system that can be easily adjusted to vary the concentration of a solution based upon an end use.

These and/or other objects, features, and advantages of the present invention will be apparent to those skilled in the art. The present invention is not to be limited to or by these objects, features and advantages. No single embodiment need provide each and every object, feature, or advantage.

According to an aspect of the invention, a method for obtaining a solution from a solid product and a liquid is provided. The method includes providing a solid product in a housing of a dispenser, introducing the liquid into the housing to contact the solid product with liquid turbulence, and adjusting the liquid turbulence of the liquid based upon a characteristic of an uncontrolled condition or solid product to maintain a predetermined concentration of the solution.

The liquid turbulence may be adjusted by changing the distance between the liquid source nozzle(s) or manifold diffuse and the solid product, changing the hole diameters of the manifold diffuse, changing the hole pattern or number of holes of the manifold diffuse, changing the geometry of the holes of the diffuse, or changing the flow rate of the liquid. Characteristics affecting the turbulence or concentration may include the density of the solid product, temperature of the liquid, distance between the liquid and the solid product, or the surface area of the product being contacted by the liquid. The turbulence may be changed automatically or manually based upon the characteristic. Furthermore, the turbulence can be altered based upon known relationships. For example, a known erosion rate may be determined for a liquid having a certain temperature. The turbulence, such as the distance between the manifold diffuse and the solid product, can be altered based upon known erosion rates to accommodate or account for the temperature of the liquid.

According to another aspect of the invention, a dispenser configured to obtain a solution from a solid product and a liquid is provided. The dispenser includes a housing, a cavity within the housing for holding a solid product, and a liquid source adjacent the cavity for providing a liquid to contact the solid product to create a solution. The liquid source comprises a liquid turbulence control to control the turbulence of the liquid contacting the solid product based upon a characteristic of the turbulence or solid product. An outlet is adjacent the cavity for discharging the solution from the dispenser.

According to yet another aspect of the invention, a method of controlling the concentration of a solution of a solid product and a liquid dispensed from a dispenser is provided. The method includes providing a solid product in a dispenser, contacting the solid product with a liquid having a liquid turbulence to produce a solution, measuring the concentration of the solution, and adjusting the liquid turbulence of the liquid based upon the measured concentration of the solution to provide a desired concentration of the solution.

DETAILED DESCRIPTION OF THE PREFERRED EMBODIMENTS

Figure 1A:
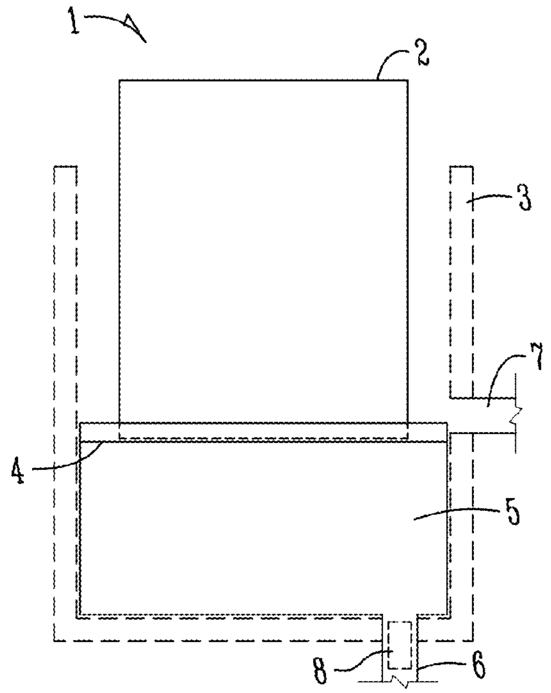
FIG. 1A is a schematic representation of one method for dispensing a solution from solid product.

The present invention relates to dispensing a liquid product obtained from a solid product. Various embodiments of the present invention will be described with reference to the drawings, wherein like reference numerals represent like parts throughout the several views. Reference to various embodiments does not limit the scope of the invention. Figures represented herein are not limitations of the various embodiments according to the inventions and are presented for exemplary illustration of the invention only.

Figure 1B:
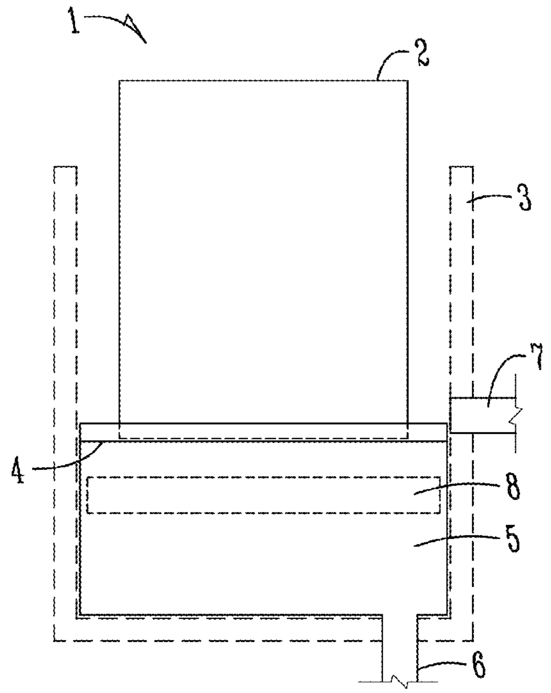
FIG. 1B is a schematic representation of another method for dispensing a solution from solid product.
Figure 1C:
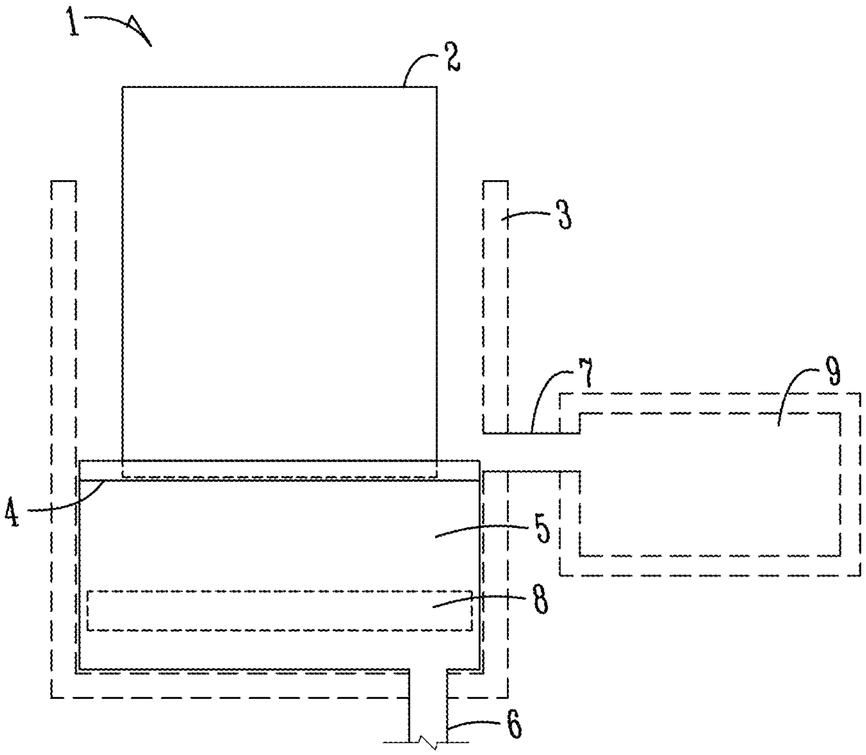
FIG. 1C is a schematic representation of another method for dispensing a solution from solid product.

FIGS. 1A-1C illustrate by schematic representations variations of a concept of the present invention for obtaining a liquid solution or liquid product from a solid product by eroding and dissolving the solid product into a liquid product or solution. In accordance with the objectives of the present invention, the schematic illustrations represent the concept of solid product erosion by controlling liquid turbulence, which may also be known as flow schemes, from a liquid source, with the liquid being in contact with a surface of a solid product. The various features and/or components shown in FIGS. 1A-1C are shown with the intent to present the overarching concept of the present invention; the production of a liquid solution or product from a solid product by controlled erosion and dissolution of the solid product using a liquid source having a controlled liquid turbulence. These objectives can be achieved at least by providing a dispenser 1 having some means for holding liquid 3.

Examples of types of liquid turbulence may include changing the flow rate of the liquid, changing the direction, flow path, or spray type of the liquid, changing the distance between liquid source and solid product, changing the amount of surface area of the solid product being exposed to the liquid (either in a pool or by spray), changing the size, number or geometry of holes associated with the spray, or the like. It should be appreciated that other changes to the turbulence of the liquid are included in the invention, and the above list is not an exhaustive one.

Furthermore, the turbulence of the liquid can be adjusted either manually or in real time to aid in maintaining the concentration of the solution created by the liquid and solid product. The turbulence can be adjusted according to a characteristic of the solid product or the liquid. For example, the turbulence can be adjusted to account for the temperature of the liquid in contact with the solid product, the flow rate of the liquid, the measured concentration of the solution, the density of the solid product, the surface area/erosion aspect of the solid product, or the like. It is contemplated that the present invention maintains a desired concentration of the solution by adjusting the turbulence based upon a characteristic. For example, if the measured concentration of the solution is not within an acceptable range, or if a measured, uncontrolled characteristic of the system is determined to be different, the dispenser can be adjusted to adjust the turbulence of the liquid to account for this, and to bring the concentration of the solution within the acceptable range. This may be done by changing the, changing the flow rate, changing the distance between the solid product and a liquid source, changing the spray type, or the like. The change in turbulence will be continued until the concentration is within an acceptable range, or until the known relationship between the measured characteristic and the erosion rate of the solid product has been accounted for to obtain a solution within an acceptable concentration. Thus, the invention contemplates the adjustment of the turbulence in real time or manually.

The liquid holding means 3 generally includes one or more walls connected to provide a basin where liquid can be introduced and used to provide erosion and dissolution of a solid product 2. The liquid holding means 3 may have vertical or horizontal configurations, or other configurations, to allow a solid product 2 to be received into contact with a pool of liquid 5 within the liquid holding means 3. Accordingly, the solid product 2 may be introduced into a dispenser 1 oriented vertically, horizontally, or in another orientation to facilitate contact of the solid product 2 with the pool of liquid 5 or liquid turbulence within the liquid holding means 3. The dispenser 1 also includes an inlet 6 for supplying liquid from a source for creating a turbulence or pool of liquid 5 within the liquid holding means 3. The dispenser 1 also includes an outlet 7 whereby a liquid product is dispensed from the dispenser 1. Placement of the outlet 7 may be used to control the amount of surface area of the solid product 2 that is in contact with the turbulence or pool of liquid 5, as well as the amount of product dispensed. Thus, liquid is introduced through inlet 6 into the dispenser 1 to obtain a liquid turbulence or pool of liquid 5. Liquid product obtained from eroding and dissolving the solid product 2 is dispensed out the outlet 7. The dispenser 1 also includes support means 4 for supporting the solid product 2 within the dispenser 1. At least one surface, edge or feature of the solid product 2 rests on the support means 4. The support means 4 is configured to allow liquid to contact a surface or surfaces of the solid product 2.

The surface or surfaces of the solid product 2 that are in contact with the turbulence or pool of liquid 5 are eroded and dissolved to obtain a liquid product from the solid product 2. Erosion and dissolution of the solid product 2 into a liquid product is obtained by controlling the liquid flow scheme or turbulence within the pool of liquid 5 or by a liquid source. The present invention contemplates various techniques for controlling the liquid flow schemes within the pool of liquid 5, and thereby controlling the rate of erosion and dissolution of the solid product 2 into a liquid product or solution. Controlling the liquid flow scheme within the pool of liquid 5 controls how the water impinges on the surface or surfaces of the solid product 2 that are in contact with the liquid 5. One means for controlling the liquid flow scheme 8 of the liquid 5 is shown in FIG. 1A. For example, means for controlling the liquid flow scheme 8 may be included in or at the inlet 6. A means for controlling the liquid flow scheme 8 within the pool of liquid 5 may also be included within the pool of liquid 5 as illustrated in FIGS. 1B and 1C.

Also, as further illustrated in FIGS. 1B-1C, the means for controlling the liquid flow scheme 8 of the liquid 5 may be moved manually or automatically to change the liquid flow scheme or turbulence of the liquid 5 and the rate of erosion and dissolution of the solid product 2 into liquid product. The means for controlling the liquid flow scheme 8 of the liquid 5 may include one or more fluid directing geometries within the pool of liquid 5. The means for controlling the liquid flow scheme 8 of the liquid 5 may also include one or more geometries or features in contact with and/or within the pool of liquid 5 or the inlet 6 that include one or more geometries that are struck by or allow liquid to flow through them to control the liquid flow scheme within the pool of liquid 5. The rate at which 1 strikes, flows through, or is affected by the means for controlling the liquid flow scheme 8 within the pool of liquid 5 may also be changed. The means for controlling the liquid flow scheme 8 within the pool of liquid 5 may be changed manually or automatically to maintain a desired concentration for the liquid product being dispensed (notwithstanding the changes in the liquid introduced into the dispenser 1 that may result from the install location of the dispenser 1). For example, spray geometry may change, the pressure of the liquid may change, or the flow rate of the liquid may change between install locations of the dispenser 1.

Accordingly, the means for controlling the liquid flow scheme 8 within the pool of liquid 5 is adjustable manually or automatically to achieve a desired rate of erosion and dissolution of the solid product 2 into liquid product notwithstanding the install location of the dispenser 1. This may be achieved by moving or altering the means for controlling the liquid flow scheme 8 of the liquid 5. Altering the means for controlling the liquid flow scheme 8 of the liquid 5 changes the way that the liquid impinges upon the surface or surfaces of the solid product 2 in contact with the pool of liquid 5. The liquid product obtained from erosion and dissolution of the solid product 2 is dispensed from the dispenser 1 through an outlet 7, such as to some end-use application 9 as illustrated in FIG. 1C. Thus, by placement of a surface or surfaces of the solid product 2 in contact with the liquid 5 within the dispenser 1, liquid flow schemes of the liquid 5 may be controlled by means for controlling the liquid flow scheme 8 to control the rate at which the solid product 2 is eroded and dissolved into a liquid product.

Figure 2:
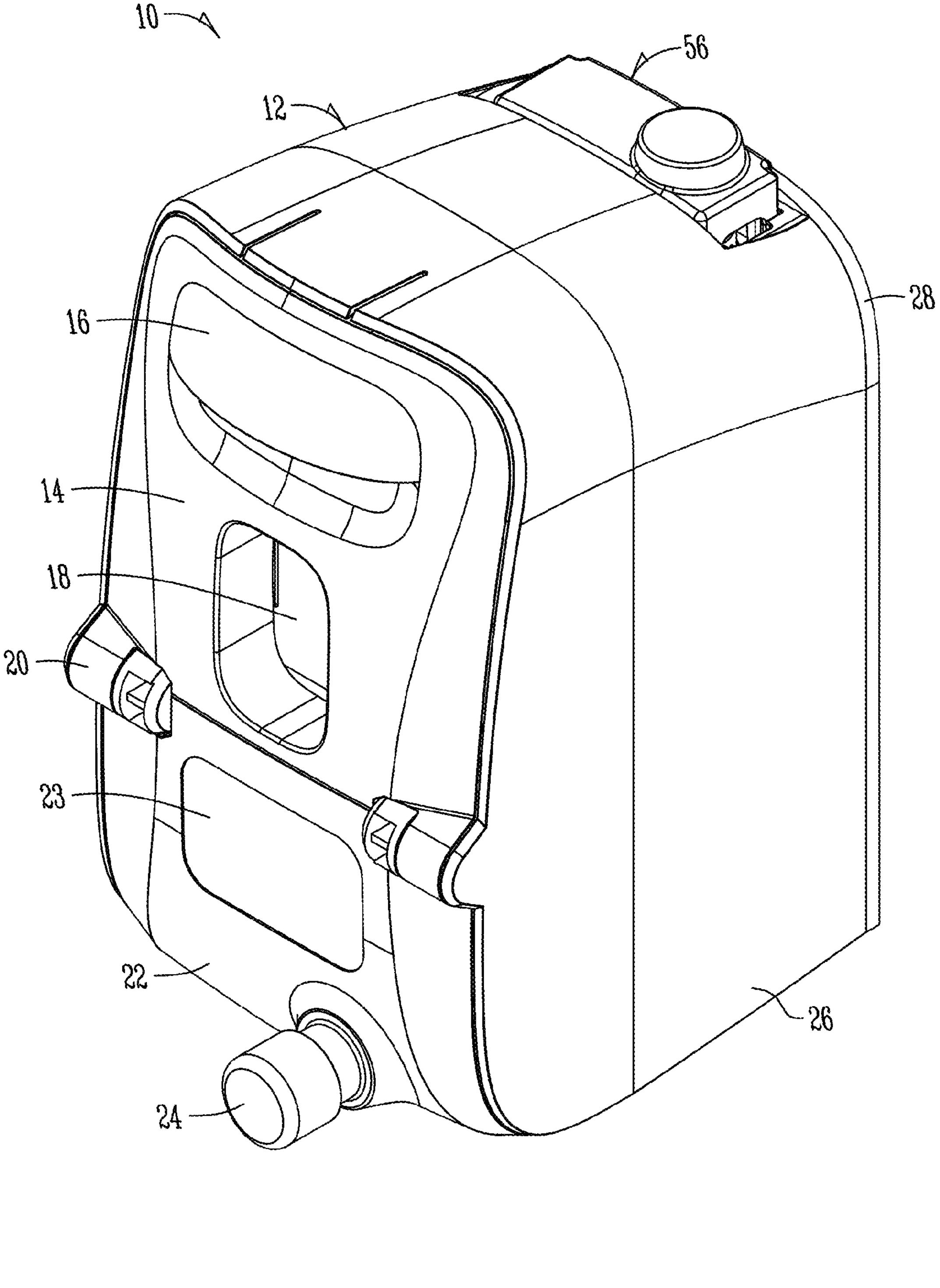
FIG. 2 is a perspective view of an embodiment of a dispenser according to the present invention.

FIG. 2 is a perspective view of an embodiment of a dispenser 10 according to the present invention. The dispenser 10 is configured to hold a solid product that is combined with a liquid, such as water, to create a solution. For example, the solid product may be mixed with the liquid to create a cleaning detergent. The dispenser works by having the liquid interact with the solid product to form a solution having a desired concentration for its end use application. The liquid may be introduced to a bottom or other surface of the solid product, as will be discussed in greater detail below. However, as mentioned, a problem can exist in obtaining and/or maintaining a desired concentration of the solution.

Therefore, the dispenser 10 of the invention includes a novel turbulence or flow scheme that is adjustable either manually or in real time based on a characteristic of either the solid product or another uncontrolled condition, such as an environmental condition. As mentioned, the characteristic may be the density of the solid product, the temperature of the liquid, the climate (humidity, temperature, pressure, etc.) of the room in which the dispenser or solid product is placed, the type of liquid used, the number of solid products used, or some combination thereof. The dispenser 10 is able to determine, based on the characteristic and the existing flow scheme or turbulence, whether the end solution comprises a concentration within an acceptable range. This may be accomplished by the use of known relationships between the characteristic and the erosion rate of the solid product, as well as the relationship between different types of turbulence and the erosion rate of the solid product. If the concentration is outside of the acceptable range, the system is manually adjusted or automatically adjusts an aspect of the turbulence of the liquid to try to get the concentration within the acceptable range.

For example, the dispenser may be adjusted to change the flow rate of the liquid coming in contact with the solid product, the distance between the liquid source nozzle and the solid product, the type of spray or pooling of the to account for more or less surface of the solid product being in contact with the liquid, or some combination thereof. The dispenser will continue to adjust this turbulence until the concentration of the solution is within an acceptable range. The turbulence is adjusted based upon known relationships between the characteristic(s) and the dispense rate of the solid chemistry. For example, by understanding the rate change of product dispense per change in degree of liquid temperature change, the turbulence can be adjusted to counteract the temperature change. The concentration is adjusted according to known relationships between the erosion or dispense rate and either the characteristic or the turbulence.

According to an exemplary embodiment, the dispenser 10 of FIG. 2 includes housing 12 comprising a front door 14 having a handle 16 thereon. The front door 14 is hingeably connected to a front fascia 22 via hinges 20 therebetween. This allows the front door 14 to be rotated about the hinge 20 to allow access into the housing 12 of the dispenser 10. For example, the front door 14 includes a window 18 therein to allow an operator to view the solid product housed within the housing 12. Once the housed product has been viewed to have eroded to a certain extent, the front door 14 can be opened via the handle to allow an operator to replace the solid product with a new un-eroded product.

The front fascia 22 may include a product ID window 23 for placing a product ID thereon. The product ID 23 allows an operator to quickly determine the type of product housed within the housing 12 such that replacement thereof is quick and efficient. The ID 23 may also include other information, such as health risks, manufacturing information, date of last replacement, or the like. Also mounted to the front fascia 22 is a button 24 for activating the dispenser 10. The button 24 may be a spring-loaded button such that pressing or depressing of the button activates the dispenser 10 to discharge an amount of solution created by the solid product and the liquid. Thus, the button 24 may be preprogrammed to dispense a desired amount per pressing of the button, or may continue to discharge an amount of solution while the button is depressed.

Connected to the front fascia 22 is a rear enclosure 26 generally covering the top, sides, and rear of the dispenser 10. The rear enclosure 26 may also be removed to access the interior of the dispenser 10. A mounting plate 28 is positioned at the rear of the dispenser 10 and includes means for mounting the dispenser to a wall or other structure. For example, the dispenser 10 may be attached to a wall via screws, hooks, or other hanging means attached to the mounting plate 28.

The components of the housing 12 of the dispenser 10 may be molded plastic or other materials, and the window 18 may be a transparent plastic such as clarified polypropylene or the like. The handle 16 can be connected and disconnected from the front door 14. In addition, a backflow prevention device 56 may be positioned at or within the rear enclosure 26 to prevent backflow of the solution.

Figure 3:
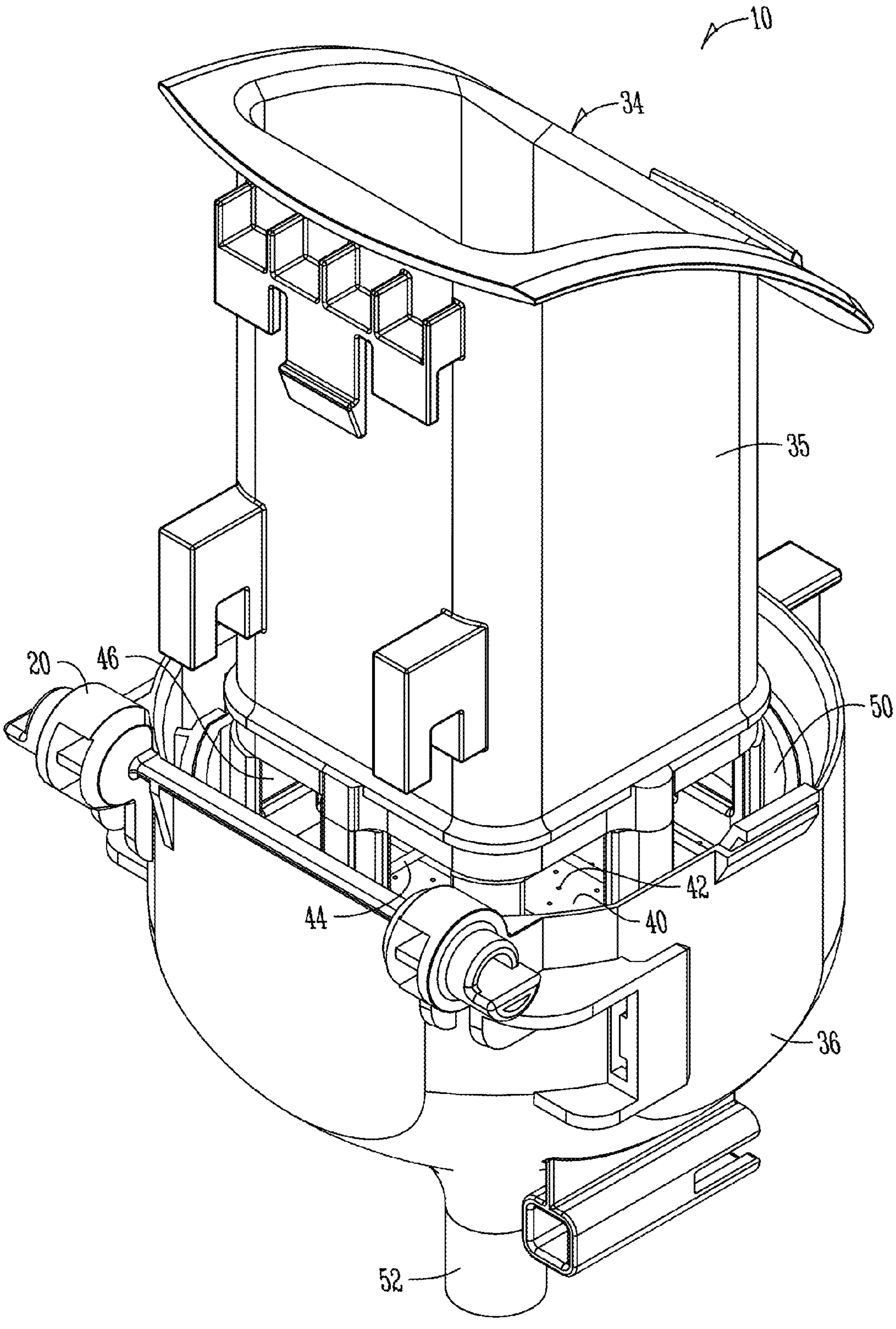
FIG. 3 is a perspective view of the dispenser of FIG. 2 with the outer housing removed.

FIG. 3 is a perspective view of the dispenser 10 of FIG. 2 with the outer housing 12 removed. Therefore, the Figure shows a perspective view of the interior components of the dispenser 10. However, it is noted that a splash guard 48 has been removed in order to see more of the components. The dispenser 10 includes a cavity or solid product holder 34 attached to a collection zone 36, which is shown to be a funnel type member. The solid product holder 34 includes plurality of cavity walls 35 extending to form an enclosure for holding a solid product. The solid product (not shown) is positioned within the cavity 34 and can rest on a support member 44, such as a product grate. The support member or grate 44 can be of any configuration and can include a number of geometries to adjust the geometry of the flow path of the liquid in contact with the solid product. It is also contemplated that a separate grate can be positioned on the support member 44 to adjust the flow geometry. For example, if it is determined that a change needs to be made to account for a change in a characteristic, it is contemplated that a new or additional grate could be positioned between the solid product and the liquid to adjust the flow geometry thereof to increase or decrease the amount of product erosion. This could be done quickly and easily in the field by an operator or technician. The grates could be varied by adjusting the size of any holes therethrough, adjusting the geometry and number of the holes, adjusting the material used for the grate, or the like to adjust the turbulence of the liquid.

Adjacent the support member 44 is shown to be a manifold diffuse 40 including a plurality of ports 42 therethrough. As will be discussed in greater detail, the ports 42 of the manifold diffuse 40 allows a liquid to pass therethrough and can be adjusted to adjust the turbulence of the liquid being in contact with a portion of the solid product stored or positioned within the cavity 34. The ports can be varied such that any size, number, or geometry of the ports is used to adjust the turbulence of the liquid therethrough. Also shown in FIG. 3 is an overflow port 46, which is used to move the formed solution from adjacent the solid product and into the collection zone 36. Therefore, the solution collector 50 will contain the formed solution until it has passed through the overflow port 46 and into the collection zone 36. From there, the solution can be passed through the discharge outlet 52 at the bottom of the collection zone 36.

Figure 4:
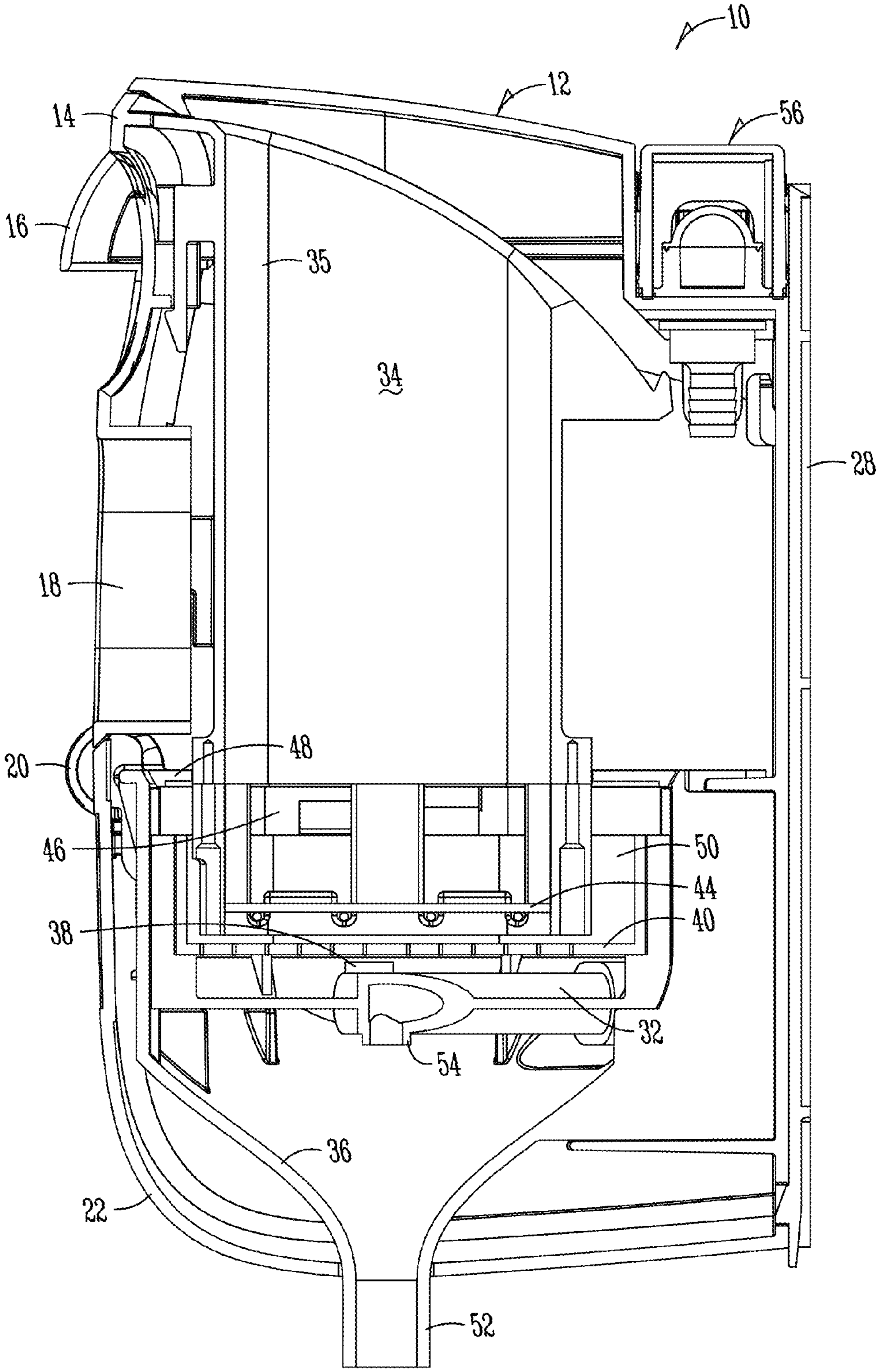
FIG. 4 is a side sectional view of the dispenser of FIG. 2.
Figure 5:
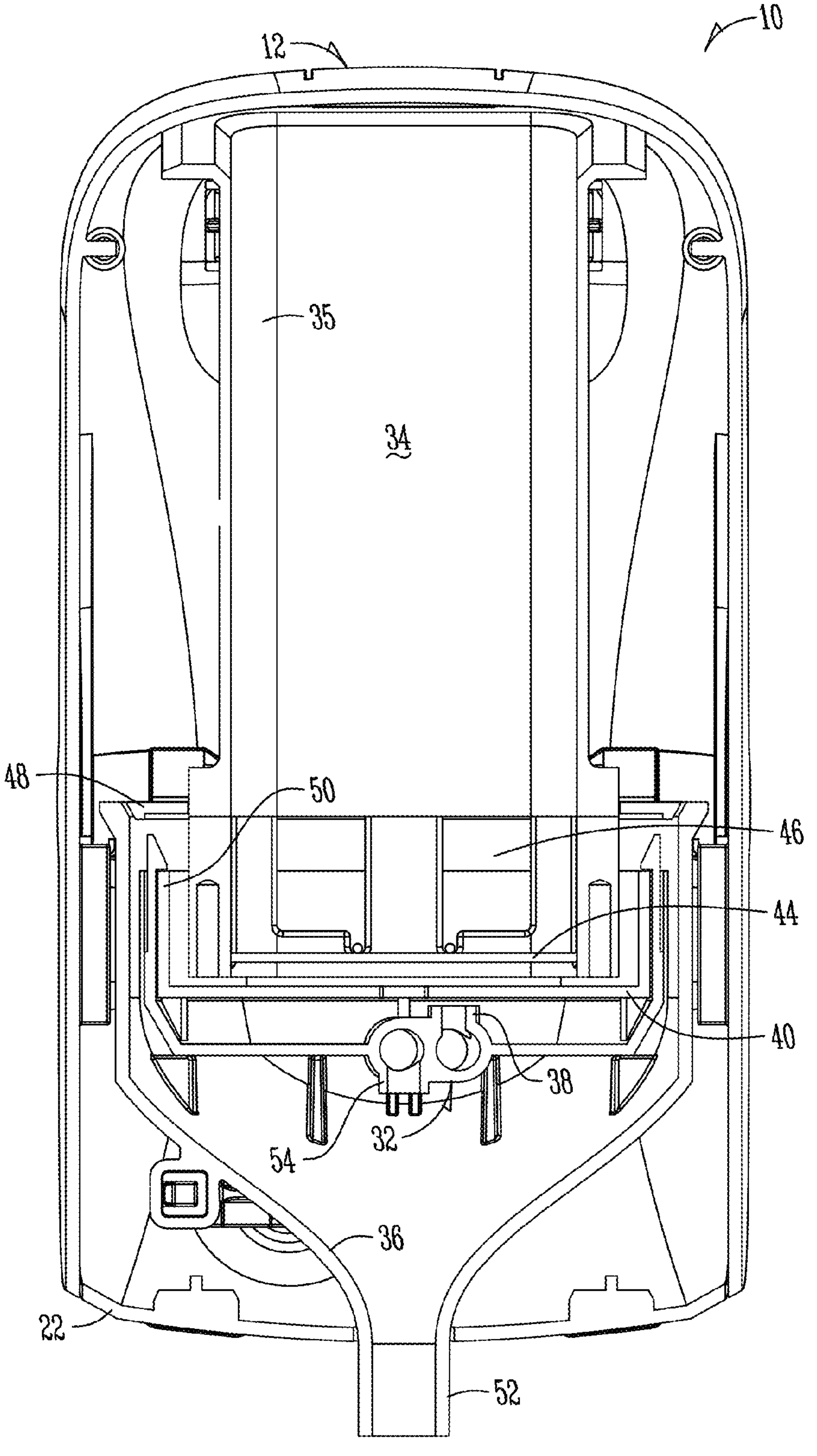
FIG. 5 is a rear sectional view of the dispenser of FIG. 2.
Figure 6:
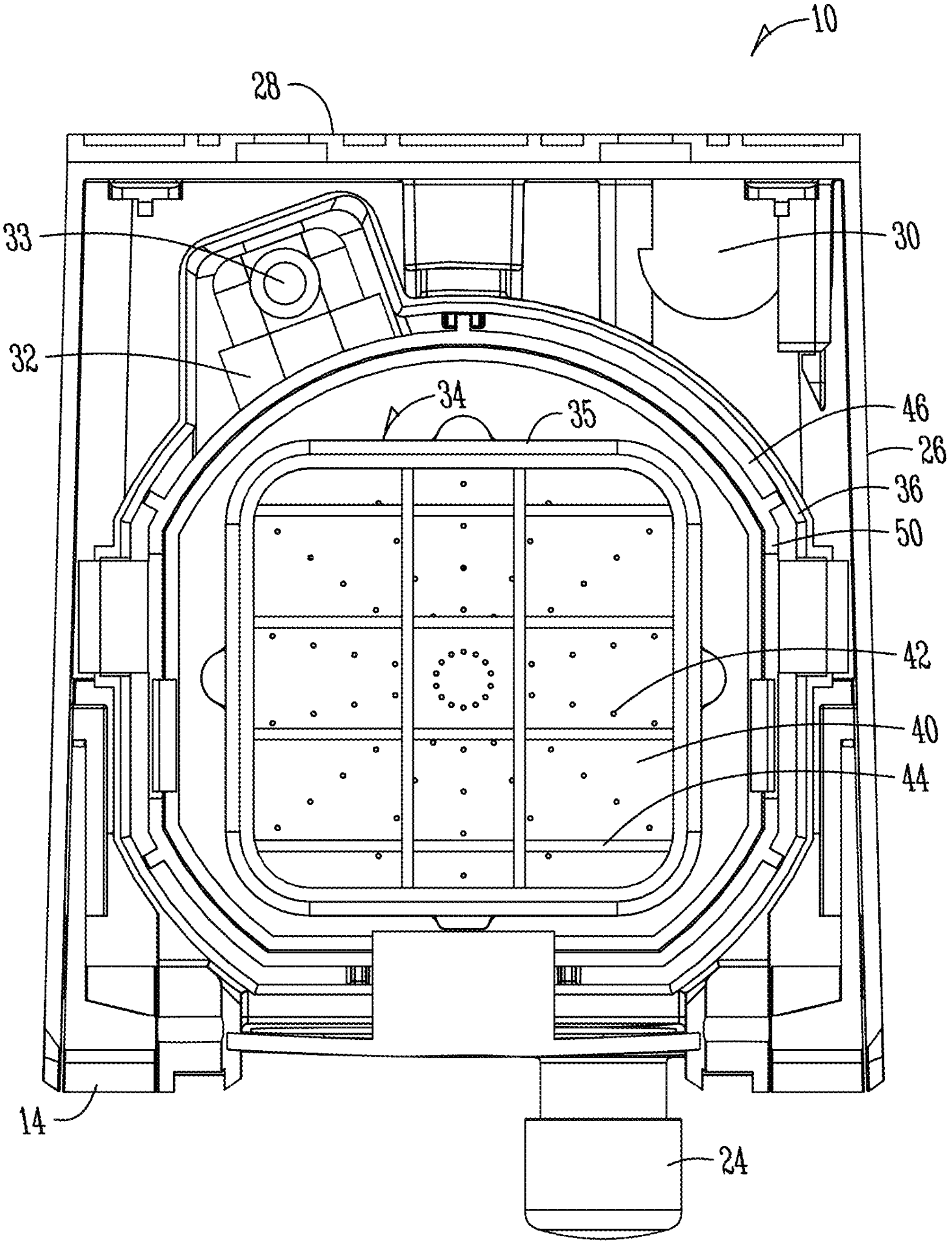
FIG. 6 is a top sectional view of the dispenser of FIG. 2.
Figure 7:
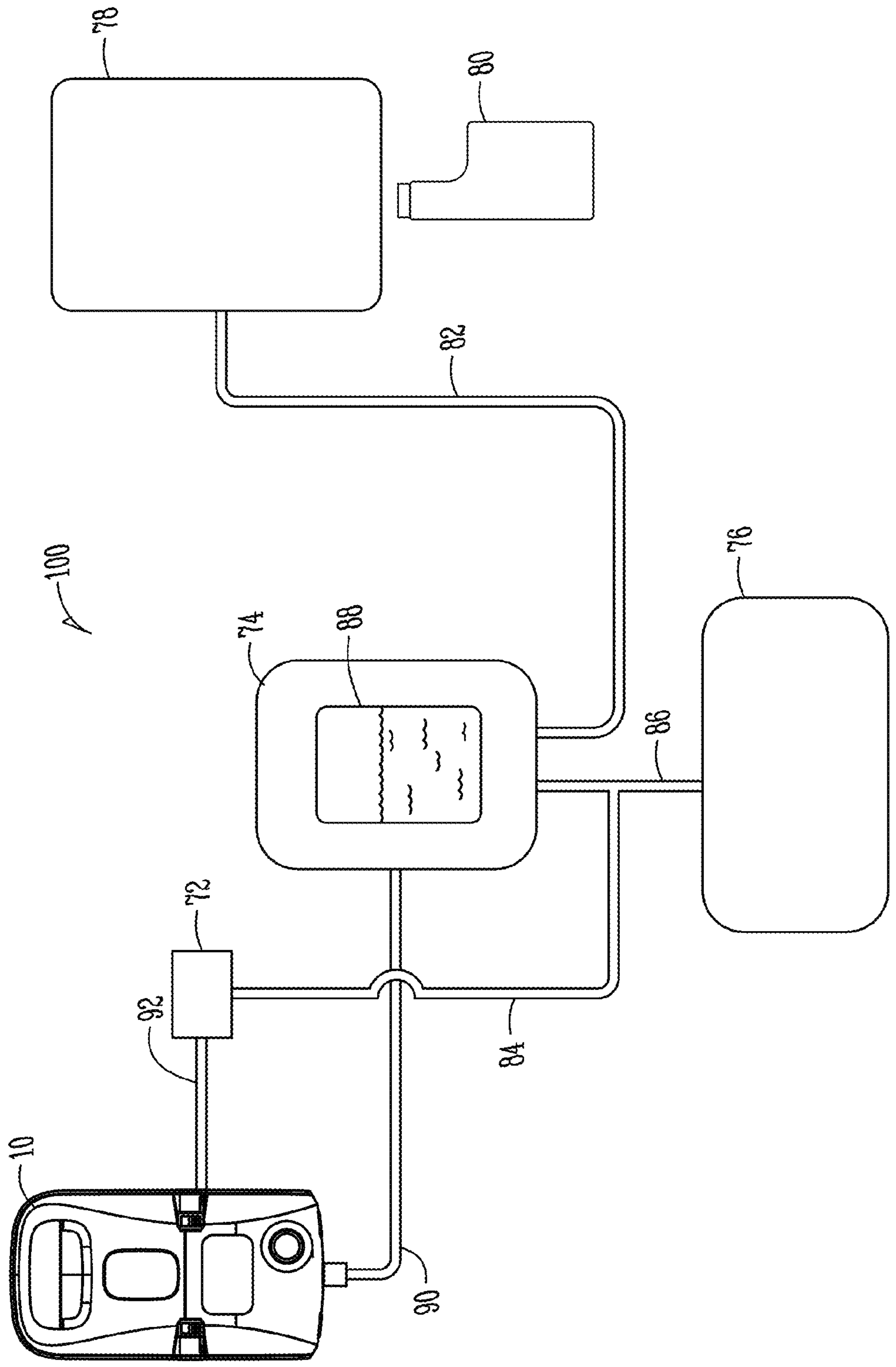
FIG. 7 is an illustration of a dispensing system incorporating the dispenser shown FIG. 2 according to an embodiment of the present invention.

FIGS. 4-6 are side, rear and top sectional views of the dispenser 10 according to an embodiment of the present invention. As discussed, a solid product is placed within the cavity 34, which is surrounded by walls 35. The solid product is placed on a support member 44, which is shown to be a product grate comprising interlocking wires. A liquid, such as water, is connected to the dispenser 10 via the liquid inlet 30 shown in FIG. 6 on the bottom side of the dispenser 10. The liquid is connected to the button 24 such that pressing the button will pass liquid into the dispenser 10 to interact and come in contact with the solid product. The liquid is passed through a liquid source 32 via a fitment splitter 33. As shown, the liquid source 32 is a split two channel liquid source for different flow paths. Each of the paths contains a flow control to properly distribute liquid in the intended amounts. As discussed, this flow control can be changed to alter the turbulence of the liquid coming in contact with the solid product to adjust the turbulence based on the characteristics to maintain the formed solution within an acceptable range of concentration. For example, the liquid may pass through the liquid source 32 and out the liquid source nozzle 38, as best shown in FIG. 4. The liquid source nozzle 38 is positioned adjacent the manifold diffuse 40 such that the liquid passing through the liquid nozzle 38 will be passed through the ports 42 of the manifold diffuse 40. The liquid will continue in a generally upwards orientation to come in contact with a portion or portions of the solid product supported by the product grate 44. The mixing of the liquid and the solid product will erode the solid product of which will dissolve portions of the solid product in the liquid to form a solution. This solution will be collected in the solution collector 50, which is generally a cup shape member having upstanding walls and bottom floor comprising the manifold diffuse 40. The solution will continue to rise in the solution collector 50 until it reaches the level of the overflow port 46, which is determined by the height of the wall comprising the solution collector 50. According to an aspect, the solution collector 50 is formed by the manifold diffuse 40 and walls extending upward therefrom. The height of the walls determines the location of the overflow port 46. The solution will escape or be passed through the overflow port 46 and into the collection zone 36, in this case a funnel. The liquid source 32 includes a second path, which ends with the diluent nozzle 54. Therefore, more liquid may be added to the solution in the collection zone 36 to further dilute the solution to obtain a solution having a concentration within the acceptable range.

Other components of the dispenser 10 include a splash guard 48 positioned generally around the top of the collection zone 36. The splash guard 48 prevents solution in the collection zone 36 from spilling outside the collection zone 36.

As stated, one advantage of the dispenser 10 according to the present invention includes the ability to make adjustments in order to obtain and maintain a desired solution having a concentration within an acceptable or predetermined range. This is generally accomplished by adjusting the turbulence of the liquid out of the liquid source nozzle 38 or that is passed through the ports 42 of the manifold diffuse 40 that is in contact with a portion of the solid product. For example, as shown and discussed, the liquid source nozzle 38 is positioned under the manifold diffuse 40. If a measured characteristic of the solid product (e.g. density, chemistry, size, etc.) or environment (liquid temperature, room climate, etc.) is determined to be different, or if the concentration of the solution in the collection zone 36 is not within the acceptable range of concentration, the turbulence of the liquid out of the liquid nozzle 38 or through the ports 42 will be adjusted. Ways to adjust the turbulence of the liquid are to adjust the distance between the liquid source nozzle 38 and the manifold diffuse 40 or the solid product, or to adjust the distance between the manifold diffuse 40 and the solid product. The dispenser may include means, such as pistons or plungers, to move either the support member 44 or the manifold diffuse 40 either closer to or away from the liquid source nozzle 38, or closer to or away from the solid product. This will alter how the water is passed through the manifold diffuse 40 and into contact with the solid product.

Furthermore, the flow rate of the liquid through the liquid nozzle 38 may be adjusted to increase or decrease the flow rate in order to increase or decrease the amount of erosion of the solid product by the liquid, which will then adjust the concentration of the solution formed between the liquid and the eroded portion of the solid product.

It is contemplated that the dispenser 10 could include an intelligent control and other means to automatically measure concentration of the solution in the collection zone 36 or to make other measurements of characteristics. These other characteristics may be the determination of the density of the solid product within the cavity 34, the temperature of the liquid passing through the liquid source 38, the amount of surface area of the solid product in contact with the liquid, the pressure of the liquid, the chemical makeup of the liquid source (hardness, alkalinity, acidity, etc.) some combination thereof, or the like. This is not intended to be an exhaustive list of characteristics that is being monitored by the dispenser 10. However, these characteristics determined by the intelligent control of the dispenser 10 will in turn cause the turbulence of the liquid passing through the liquid nozzle 38 to be adjusted to account for the characteristics in order to obtain and maintain a solution having a desired concentration. For example, if the dispenser 10 determines that the temperature of the liquid passing through the liquid nozzle 38 will cause the solid product to erode at a faster rate, the dispenser 10 may move the solid product further away from the liquid nozzle 38 in order to slow down the erosion of the solid product to maintain the concentration of the solution form therein. This is determined based upon known relationships between the temperature and erosion rate, as well as the relationship between distance and erosion rate. In addition, if the solution measured in the collection zone 36 is deemed to have a higher concentration than is acceptable, additional liquid can be passed through the diluent liquid nozzle 54, which passes the liquid directly into the collection zone 36 in order to further dilute the solution and to lower the concentration of the solution in the collection zone before discharging via the outlet 52.

Figure 8:
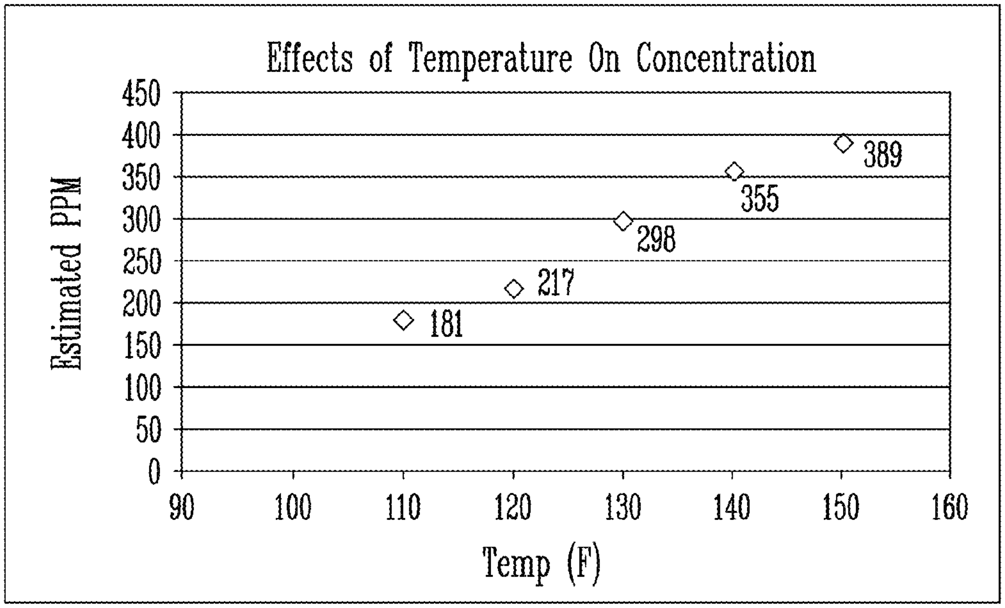
FIG. 8 is a plot illustrating the effect of temperature on concentration of the dispensed solution.
Figure 9:
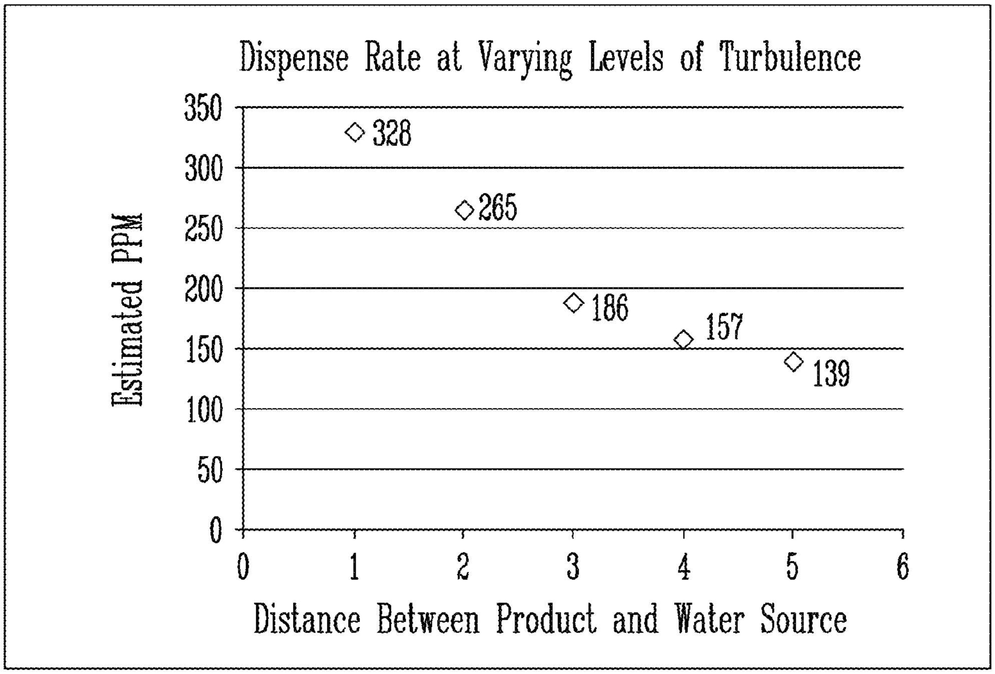
FIG. 9 is a plot illustrating the effect of distance between the diffusion manifold and the solid product on concentration of the dispensed solution.

FIGS. 8 and 9 are plots illustrating the known relationships of temperature and distance on the concentration of the dispensed solution. It should be noted that these plots are for illustrative purposes only, and are not to be the only data used to determine the concentration and to adjust the turbulence. Any other known relationships between characteristics, turbulence, and concentration may be used and are contemplated to be a part of the present invention. For example, a plot showing the relationship between the flow rate, force, or other change and the erosion rate of a chemistry could be used to adjust the dispenser based upon known or tested results. FIG. 8 is a plot illustrating the effect of temperature on concentration of the dispensed solution. As has been discussed, the temperature of the liquid acting on the solid product is one characteristic that the dispenser 10 of the present invention will be determining to continuously adjust the turbulence of the liquid to account for an acceptable concentration of the solution. FIG. 8 shows an example of how exactly the temperature of the liquid can affect the rate of erosion of the solid product. As can be expected, the higher the temperature of the liquid, the higher the rate of erosion and higher the concentration of the solution. Therefore, if the dispenser determines that the temperature of the liquid source is higher or at a certain temperature, the dispenser can adjust other characteristics, such as the distance between the liquid nozzle 38 and the solid product in order to limit the amount of erosion, and thus limit the concentration of the solution form.

As shown in FIG. 9, as the distance between the product and the liquid source is increased, the erosion rate and thus, the concentration of the solution formed are lowered. Therefore, viewing the two plots shown in FIGS. 8 and 9 can show that if the temperature is within a higher range, the distance between the manifold diffuse 40 and the liquid product should also be increased in order to account for the higher temperature. This is but one example of how the dispenser may take a determination of a characteristic of the liquid or the solid product and to adjust the turbulence or flow scheme of the liquid in order to maintain the concentration of the solution within an acceptable range.

Thus, the dispenser shown and described includes an adjustment means to obtain and maintain a concentration of the solution, and to monitor characteristics of the system to adjust the turbulence of the liquid being dispensed into contact with the solid product in order to maintain a solution in the collection zone 36 having an acceptable concentration. This can be very important as some characteristics are not as controllable as others. For example, some solid products may have varying densities, even if the products comprise the same chemistry. The length of time of being stored, the climate of storage, or the like can alter the characteristics of the solid products such that it will affect the density thereof. Thus, one single type of flow scheme or turbulence being in contact with the varying solid products may not always result in the same concentration of the solution. Therefore, the dispenser 10 of the present invention allows for this to be monitored, which will allow the dispenser to make adjustments based on the varying characteristics of the environment and of the solid product in order to continuously provide a solution being within an acceptable range of concentration for the specific end use application.

Furthermore, according to some embodiments, as the dispenser 10 can be doing the determinations of the characteristics and making the adjustments of the turbulence, the dispenser can be more efficient, and operators' time will not need to be spent figuring out the varying characteristics for each system and then making adjustments thereon. Instead, the operator is able to replace a solid product in the dispenser, and then allow the dispenser to make the required determinations of the varying characteristics, e.g. temperature, density, distance, and the like, and to automatically update the components of the dispenser 10 to provide a discharging solution being within an acceptable range of concentration.

FIG. 9 shows a schematic of a dispensing system 100 according to an aspect of the present invention. The dispensing system 100 includes a dispenser 10 connected to a liquid supply line 92, thereby placing the dispenser 10 in communication with a liquid source 72. The liquid entering the dispenser 10 creates a concentrated solution or a liquid concentrate from a solid product stored within the dispenser 10. The solution is dispensed via liquid solution line 86. In an embodiment, the dispensed liquid solution may be captured in a sump 74. Depending upon the specific end use application 76, the specific concentration of the solution dispensed from sump 74 may be controlled by adding liquid from the liquid source 72 through a liquid makeup line 84 to combine with the solution in the solution line 86. Thus, the concentration of the resulting solution dispensed to an end use application 76 may be adjusted using liquid from the liquid source 72 from generating a ready to use solution that, for example, is gravity fed to a sink. In another aspect of the dispensing system 100, a liquid solution may be dispensed from a sump 74 or directly from the dispenser 10 to an end use application line aspirator 78 via pickup line 82. In this aspect, a bottle applicator, such a spray bottle 80 is filled with a solution from sump 74 via pickup line 82 using aspirator 78. In this manner, a concentrated solution derived from eroding and dissolving a solid product is used in one or more end use applications. The desired concentration of the solution may be adjusted according to the desired concentration for each particular end use application. In each instance, the concentrated solution results from the erosion in dissolution of a solid product according to the aforementioned embodiments of the present invention.

Therefore, the dispenser shown and described includes but a few possible examples of ways to obtain and maintain a concentration formed by a liquid and a solid product chemistry. As noted, plots can be made based upon testing of various characteristics and changes to the liquid turbulence. The plots can be used to set up a system having parameters (geometries, distances, flow types, flow rates, etc.) that are generalized to obtain the desired concentration. Furthermore, adjustments can be made to the dispenser to account for a change one or more of the parameters, which changes the turbulence of the liquid. For example, a change in temperature of the liquid can signal a need to change the distance between the liquid and the solid product. The plot can be used to determine the distance based upon the change in temperature. In addition, many other parameters of the turbulence could be changed to account for the change in the characteristic of the solid product or the environment.

As should be appreciated, such an invention provides numerous advantages and benefits. One advantage relates to safety. The invention will provide more consistent and predictable concentrations of a solid product chemistry and a liquid, which are set to be within safe ranges. A technician or operator will have higher confidence that the solution will be what they expect. Furthermore, the system will have economic benefits, as costs can be saved by taking into account behaviors. For example, operators may have a tendency to raise the temperature of the liquid, in order to speed up a cleaning process. The dispenser of the invention will take this into account and can actually offset the temperature change by changing another aspect of the system. This will aid in a consistent erosion of the product, which can aid in the predictability for product costs, as well as budgeting aspects for expecting to know when a product will need to be changed. The uniform erosion of the solid product will provide predictable dispensing and increased business planning and/or forecasting.

The foregoing description has been presented for purposes of illustration and description, and is not intended to be an exhaustive list or to limit to the invention to the precise forms disclosed. It is contemplated that other alternative processes obvious to those skilled in the art are to be considered in the invention.

What is claimed is:

1. A method for obtaining a solution from a solid product and a liquid, comprising:
- combining the liquid and solid in a pool to form the solution, the liquid being added to the pool with a variable turbulence; and
- adjusting the turbulence of the liquid being added to the pool based upon a characteristic of the turbulence or solid product to maintain a desired concentration of the solution that is discharged from the dispenser and towards an end use application;
- wherein the pool configured to erode the solid product to form the solution.

2. The method of claim 1, further comprising continuously preparing a new solution of new liquid and solid product being formed with the adjusted liquid turbulence to obtain the desired concentration.

3. The method of claim 2, further comprising discharging the solution from the dispenser towards an end use application without the solution returning to the dispenser.

4. The method of claim 1, wherein the step of adjusting the liquid turbulence comprises changing the flow rate of the liquid contacting the solid product.

5. The method of claim 1, wherein the step of adjusting the liquid turbulence comprises changing the distance between a source of the liquid and the solid product.

6. The method of claim 1, further comprising adding the liquid to the solution to further combine the liquid and the solid product.

7. The method of claim 1, wherein the characteristic comprises:
- a. the temperature of the liquid;
- b. the chemistry of the solid product;
- c. the density of the solid product;
- d. the shape of the solid product; or
- e. the climate of the location of the solid product or dispenser.

8. The method of claim 1, further comprising discharging the solution to a sump.

9. The method of claim 8, further comprising adding additional liquid to the solution as it is dispensed from the sump and towards the end use application.

10. The method of claim 1, further comprising dispensing the solution to an aspirator for use in filling a container.

11. A method of controlling the concentration of a solution of a solid product and a liquid dispensed from a dispenser, comprising:
- combining the liquid and solid product in a pool to form the solution, the liquid being added to the pool with a variable turbulence;
- measuring the concentration of the solution; and
- adjusting the turbulence of the liquid being added to the pool based upon the measured concentration of the solution to provide a desired concentration of the solution that is discharged towards an end use application.

12. The method of claim 11, further comprising repeating the steps of contacting, measuring, and adjusting until a desired concentration of solution is obtained.

13. The method of claim 12, further comprising dispensing the desired concentration of solution from an outlet of the dispenser towards the end use application without the solution returning to the dispenser.

14. The method of claim 11, wherein the adjusting step is performed in a housing containing the solid product.

15. The method of claim 11, wherein the adjusting step occurs after an initial amount of solution has been dispensed and prior to the end use application.

16. The method of claim 11, wherein the adjusting step comprises adjusting the liquid turbulence comprises changing the flow rate of the liquid contacting the solid product or changing the distance between a source of the liquid and the solid product.

17. A dispenser configured to obtain a solution from a solid product and a liquid, comprising:
- a housing;
- a cavity within the housing for holding a solid product;
- a liquid source adjacent the cavity for providing a pool of liquid to contact the solid product to create a solution;
- wherein the liquid source comprises a variable liquid turbulence control to control the turbulence of the liquid being added to the pool and contacting the solid product based upon a characteristic of the liquid, environment climate, or solid product; and
- an outlet adjacent the cavity for discharging the solution from the dispenser and towards an end use application without having the solution return.

18. The dispenser of claim 17, further comprising a diffuse manifold positioned between the liquid source and the cavity.

19. The dispenser of claim 18, further comprising a collection zone for the solution between the cavity and outlet.

20. The dispenser of claim 19, further comprising a probe in the collection zone for determining the concentration of the formed solution.

* * * * *